United States Patent [19]

Dean et al.

[11] Patent Number: 5,720,934
[45] Date of Patent: Feb. 24, 1998

[54] TECHNETIUM-99M LABELED PEPTIDES FOR IMAGING

[75] Inventors: Richard T. Dean, Bedford; Scott Buttram, Derry; William McBride, Manchester; John Lister-James, Bedford; Edgar R. Civitello, Londonderry, all of N.H.

[73] Assignee: Diatide, Inc., Londonderry, N.H.

[21] Appl. No.: 486,135

[22] Filed: Jun. 6, 1995

Related U.S. Application Data

[62] Division of Ser. No. 871,282, Apr. 30, 1992.

[51] Int. Cl.$^6$ .................... A61K 51/00; A61M 36/14
[52] U.S. Cl. ................ 424/1.69; 424/1.65; 424/1.11; 530/300
[58] Field of Search .................. 424/1.11, 1.49, 424/1.53, 1.65, 1.69, 9.1; 534/10–16; 530/300, 324–330, 333–334, 338; 206/223, 569, 570

[56] References Cited

U.S. PATENT DOCUMENTS

| | | | |
|---|---|---|---|
| 5,371,184 | 12/1994 | Rajagopalan et al. | 530/324 |
| 5,508,020 | 4/1996 | Dean et al. | 424/1.69 |

FOREIGN PATENT DOCUMENTS

| | | |
|---|---|---|
| 9213572 | 8/1992 | WIPO |
| 9317719 | 9/1993 | WIPO |
| 9321962 | 11/1993 | WIPO |
| 9323085 | 11/1993 | WIPO |
| 9400489 | 1/1994 | WIPO |
| 9419024 | 9/1994 | WIPO |
| 9423758 | 10/1994 | WIPO |
| 9428942 | 12/1994 | WIPO |
| 9503330 | 2/1995 | WIPO |
| 9529708 | 11/1995 | WIPO |
| 9533496 | 12/1995 | WIPO |

*Primary Examiner*—John Kight
*Assistant Examiner*—Dameron Jones
*Attorney, Agent, or Firm*—McDonnell Boehnen Hulbert & Berghoff

[57] ABSTRACT

This invention relates to radiolabel binding moieties for producing radiolabeled peptides and methods for making such peptides. Specifically, the invention relates to picolinic acid or picolinamine containing radiolabel binding moieties, peptides radiolabeled therewith and methods of making and using both the radiolabel binding moieties and peptides radiolabeled therewith.

2 Claims, No Drawings

SEQUENCE LISTING ( 1 ) GENERAL INFORMATION:

( i i i ) NUMBER OF SEQUENCES: 19

( 2 ) INFORMATION FOR SEQ ID NO:1:

( i ) SEQUENCE CHARACTERISTICS:
        ( A ) LENGTH: 18 amino acids
        ( B ) TYPE: amino acid
        ( D ) TOPOLOGY: linear ( i i ) MOLECULE TYPE: peptide ( i x ) FEATURE:
        ( A ) NAME/KEY: Modified-site
        ( B ) LOCATION: 23..24
        ( D ) OTHER INFORMATION: /label=AMIDE
            / note= "The carboxyl terminus is an amide."

( x i ) SEQUENCE DESCRIPTION: SEQ ID NO:1:

Val  Gly  Val  Ala  Pro  Gly  Val  Gly  Val  Ala  Pro  Gly  Val  Gly  Val  Ala
1                   5                        10                       15

Pro  Gly ( 2 ) INFORMATION FOR SEQ ID NO:2:

( i ) SEQUENCE CHARACTERISTICS:
        ( A ) LENGTH: 20 amino acids
        ( B ) TYPE: amino acid
        ( D ) TOPOLOGY: linear ( i i ) MOLECULE TYPE: peptide ( i x ) FEATURE:
        ( A ) NAME/KEY: Modified-site -continued (B) LOCATION: 19..20
    (D) OTHER INFORMATION: /label=AMIDE
        / note= "The carboxyl terminus is an amide."

(xi) SEQUENCE DESCRIPTION: SEQ ID NO:2:

Val Pro Gly Val Gly Val Pro Gly Val Gly Val Pro Gly Val Gly Val
1               5                   10                  15

Pro Gly Val Gly
            20

(2) INFORMATION FOR SEQ ID NO:3:

(i) SEQUENCE CHARACTERISTICS:
        (A) LENGTH: 17 amino acids
        (B) TYPE: amino acid
        (D) TOPOLOGY: linear (ii) MOLECULE TYPE: peptide (ix) FEATURE:
        (A) NAME/KEY: Modified-site
        (B) LOCATION: 16..17
        (D) OTHER INFORMATION: /label=AMIDE
            / note= "The carboxyl terminus is an amide."

(xi) SEQUENCE DESCRIPTION: SEQ ID NO:3:

Arg Ala Leu Val Asp Thr Leu Lys Phe Val Thr Gln Ala Glu Gly Ala
1               5                   10                  15

Lys (2) INFORMATION FOR SEQ ID NO:4:

(i) SEQUENCE CHARACTERISTICS:
        (A) LENGTH: 17 amino acids
        (B) TYPE: amino acid
        (D) TOPOLOGY: linear (ii) MOLECULE TYPE: peptide (ix) FEATURE:
        (A) NAME/KEY: Modified-site
        (B) LOCATION: 16..17
        (D) OTHER INFORMATION: /label=AMIDE
            / note= "The carboxyl terminus is an amide."

(xi) SEQUENCE DESCRIPTION: SEQ ID NO:4:

Arg Ala Leu Val Asp Thr Glu Phe Lys Val Lys Gln Glu Ala Gly Ala
1               5                   10                  15

Lys (2) INFORMATION FOR SEQ ID NO:5:

(i) SEQUENCE CHARACTERISTICS:
        (A) LENGTH: 18 amino acids
        (B) TYPE: amino acid
        (D) TOPOLOGY: linear (ii) MOLECULE TYPE: peptide (ix) FEATURE:
        (A) NAME/KEY: Modified-site
        (B) LOCATION: 17..18
        (D) OTHER INFORMATION: /label=AMIDE
            / note= "The carboxyl terminus is an amide."

(xi) SEQUENCE DESCRIPTION: SEQ ID NO:5:

Pro Leu Ala Arg Ile Thr Leu Pro Asp Phe Arg Leu Pro Glu Ile Ala
1               5                   10                  15

Ile Pro ( 2 ) INFORMATION FOR SEQ ID NO:6:

( i ) SEQUENCE CHARACTERISTICS:
        ( A ) LENGTH: 14 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:6:

```
Gly Gln Gln His His Leu Gly Gly Ala Lys Ala Gly Asp Val
1               5                   10
```

( 2 ) INFORMATION FOR SEQ ID NO:7:

( i ) SEQUENCE CHARACTERISTICS:
        ( A ) LENGTH: 13 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:7:

```
Pro Leu Tyr Lys Lys Ile Ile Lys Lys Leu Leu Glu Ser
1               5                   10
```

( 2 ) INFORMATION FOR SEQ ID NO:8:

( i ) SEQUENCE CHARACTERISTICS:
        ( A ) LENGTH: 9 amino acids
        ( B ) TYPE: amino acid
        ( D ) TOPOLOGY: linear ( i i ) MOLECULE TYPE: peptide ( i x ) FEATURE:
        ( A ) NAME/KEY: Modified-site
        ( B ) LOCATION: 8..9
        ( D ) OTHER INFORMATION: /label=AMIDE
            / note= "The carboxyl terminus is an amide."

( x i ) SEQUENCE DESCRIPTION: SEQ ID NO:8:

```
Leu Arg Ala Leu Val Asp Thr Leu Lys
1               5
```

( 2 ) INFORMATION FOR SEQ ID NO:9:

( i ) SEQUENCE CHARACTERISTICS:
        ( A ) LENGTH: 12 amino acids
        ( B ) TYPE: amino acid
        ( D ) TOPOLOGY: linear ( i i ) MOLECULE TYPE: peptide ( i x ) FEATURE:
        ( A ) NAME/KEY: Modified-site
        ( B ) LOCATION: 11..12
        ( D ) OTHER INFORMATION: /label=AMIDE
            / note= "The carboxyl terminus is an amide."

( x i ) SEQUENCE DESCRIPTION: SEQ ID NO:9:

```
Gly Gly Gly Leu Arg Ala Leu Val Asp Thr Leu Lys
1               5                   10
```

( 2 ) INFORMATION FOR SEQ ID NO:10:

( i ) SEQUENCE CHARACTERISTICS:
        ( A ) LENGTH: 21 amino acids
        ( B ) TYPE: amino acid
        ( D ) TOPOLOGY: linear ( i i ) MOLECULE TYPE: peptide ( i x ) FEATURE:
    ( A ) NAME/KEY: Modified-site
    ( B ) LOCATION: 20..21
    ( D ) OTHER INFORMATION: /label=AMIDE
        / note= "The carboxyl terminus is an amide."

( x i ) SEQUENCE DESCRIPTION: SEQ ID NO:10:

```
Gly Gly Gly Leu Arg Ala Leu Val Asp Thr Leu Lys Phe Val Thr Gln
1               5                   10                  15

Ala Glu Gly Ala Lys
            20
```

( 2 ) INFORMATION FOR SEQ ID NO:11:

( i ) SEQUENCE CHARACTERISTICS:
        ( A ) LENGTH: 17 amino acids
        ( B ) TYPE: amino acid
        ( D ) TOPOLOGY: linear ( i i ) MOLECULE TYPE: peptide ( i x ) FEATURE:
        ( A ) NAME/KEY: Modified-site
        ( B ) LOCATION: 16..17
        ( D ) OTHER INFORMATION: /label=AMIDE
            / note= "The carboxyl terminus is an amide."

( x i ) SEQUENCE DESCRIPTION: SEQ ID NO:11:

```
Gly Gly Gly Arg Ala Leu Val Asp Thr Leu Lys Ala Leu Val Asp Thr
1               5                   10                  15

Leu
```

( 2 ) INFORMATION FOR SEQ ID NO:12:

( i ) SEQUENCE CHARACTERISTICS:
        ( A ) LENGTH: 28 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:12:

```
Gly His Arg Pro Leu Asp Lys Lys Arg Glu Glu Ala Pro Ser Leu Arg
1               5                   10                  15

Pro Ala Pro Pro Pro Ile Ser Gly Gly Gly Tyr Arg
            20                  25
```

( 2 ) INFORMATION FOR SEQ ID NO:13:

( i ) SEQUENCE CHARACTERISTICS:
        ( A ) LENGTH: 17 amino acids
        ( B ) TYPE: amino acid
        ( D ) TOPOLOGY: linear ( i i ) MOLECULE TYPE: peptide ( i x ) FEATURE:
        ( A ) NAME/KEY: Modified-site
        ( B ) LOCATION: 16..17
        ( D ) OTHER INFORMATION: /label=AMIDE
            / note= "The carboxyl terminus is an amide."

( x i ) SEQUENCE DESCRIPTION: SEQ ID NO:13:

```
Pro Ser Pro Ser Pro Ile His Pro Ala His His Lys Arg Asp Arg Arg
1               5                   10                  15

Gln
```

( 2 ) INFORMATION FOR SEQ ID NO:14:

( i ) SEQUENCE CHARACTERISTICS:
        ( A ) LENGTH: 11 amino acids
        ( B ) TYPE: amino acid
        ( D ) TOPOLOGY: linear ( i i ) MOLECULE TYPE: peptide ( i x ) FEATURE:
        ( A ) NAME/KEY: Modified-site
        ( B ) LOCATION: 4..7
        ( D ) OTHER INFORMATION: /label=Variantaas
            / note= "The phenylalanine and tryptophan residues
            are the D stereoisomers, residue X is
            L-(4- chlorophenyl) alanine, and the carboxyl terminus..."

( x i ) SEQUENCE DESCRIPTION: SEQ ID NO:14:

Gly Gly Gly Phe Xaa Tyr Trp Lys Thr Phe Thr
1               5                   10

( 2 ) INFORMATION FOR SEQ ID NO:15:

( i ) SEQUENCE CHARACTERISTICS:
        ( A ) LENGTH: 9 amino acids
        ( B ) TYPE: amino acid
        ( D ) TOPOLOGY: linear ( i i ) MOLECULE TYPE: peptide ( i x ) FEATURE:
        ( A ) NAME/KEY: Disulfide-bond
        ( B ) LOCATION: 3..9
        ( D ) OTHER INFORMATION: /label=Variant
            / note= "Residue X is L-[S-(3-aminopropyl)
            cysteine"

( x i ) SEQUENCE DESCRIPTION: SEQ ID NO:15:

Gly Gly Cys Asn Pro Xaa Gly Asp Cys
1               5

( 2 ) INFORMATION FOR SEQ ID NO:16:

( i ) SEQUENCE CHARACTERISTICS:
        ( A ) LENGTH: 12 amino acids
        ( B ) TYPE: amino acid
        ( D ) TOPOLOGY: linear ( i i ) MOLECULE TYPE: peptide ( i x ) FEATURE:
        ( A ) NAME/KEY: Modified-site
        ( B ) LOCATION: 11..12
        ( D ) OTHER INFORMATION: /label=AMIDE
            / note= "The carboxyl terminus is an amide."

( x i ) SEQUENCE DESCRIPTION: SEQ ID NO:16:

Gly Gly Gly Leu Arg Ala Leu Val Asp Thr Leu Lys
1               5                   10

( 2 ) INFORMATION FOR SEQ ID NO:17:

( i ) SEQUENCE CHARACTERISTICS:
        ( A ) LENGTH: 14 amino acids
        ( B ) TYPE: amino acid
        ( D ) TOPOLOGY: linear ( i i ) MOLECULE TYPE: peptide ( i x ) FEATURE:
        ( A ) NAME/KEY: Modified-site
        ( B ) LOCATION: 11..12

-continued (D) OTHER INFORMATION: /label=AMIDE
/ note= "The carboxyl terminus is an amide."

( x i ) SEQUENCE DESCRIPTION: SEQ ID NO:17:

Gly Cys Gly Gly Gly Leu Arg Ala Leu Val Asp Thr Leu Lys
1               5                   10

( 2 ) INFORMATION FOR SEQ ID NO:18:

( i ) SEQUENCE CHARACTERISTICS:
(A) LENGTH: 20 amino acids
(B) TYPE: amino acid
(D) TOPOLOGY: linear ( i i ) MOLECULE TYPE: peptide ( i x ) FEATURE:
(A) NAME/KEY: Modified-site
(B) LOCATION: 19..20
(D) OTHER INFORMATION: /label=AMIDE
/ note= "The carboxyl terminus is an amide."

( x i ) SEQUENCE DESCRIPTION: SEQ ID NO:18:

Gly Cys Tyr Arg Ala Leu Val Asp Thr Leu Lys Phe Val Thr Gln Ala
1               5                   10                  15
Glu Gly Ala Lys
            20

( 2 ) INFORMATION FOR SEQ ID NO:19:

( i ) SEQUENCE CHARACTERISTICS:
(A) LENGTH: 20 amino acids
(B) TYPE: amino acid
(D) TOPOLOGY: linear ( i i ) MOLECULE TYPE: peptide ( i x ) FEATURE:
(A) NAME/KEY: Modified-site
(B) LOCATION: 19..20
(D) OTHER INFORMATION: /label=AMIDE
/ note= "The carboxyl terminus is an amide."

( x i ) SEQUENCE DESCRIPTION: SEQ ID NO:19:

Gly Cys Val Gly Val Ala Pro Gly Val Gly Val Ala Pro Gly Val Gly
1               5                   10                  15
Val Ala Pro Gly
            20

TECHNETIUM-99M LABELED PEPTIDES FOR IMAGING

This is a divisional of application Ser. No. 07/871,282, filed Apr. 30, 1992.

BACKGROUND OF THE INVENTION

1. Field of the Invention

This invention relates to radiodiagnostic reagents and peptides, and methods for producing labeled radiodiagnostic agents. Specifically, the invention relates to peptides, methods and kits for making such peptides, and methods for using such peptides to image sites in a mammalian body labeled with technetium-99m (Tc-99m) via a radiolabel-binding moiety which forms a neutral complex with Tc-99m.

2. Description of the Prior Art

In the field of nuclear medicine, certain pathological conditions are localized, or their extent is assessed, by detecting the distribution of small quantities of internally-administered radioactively labeled tracer compounds (called radiotracers or radiopharmaceuticals). Methods for detecting these radiopharmaceuticals are known generally as imaging or radioimaging methods.

In radioimaging, the radiolabel is a gamma-radiation emitting radionuclide and the radiotracer is located using a gamma-radiation detecting camera (this process is often referred to as gamma scintigraphy). The imaged site is detectable because the radiotracer is chosen either to localize at a pathological site (termed positive contrast) or, alternatively, the radiotracer is chosen specifically not to localize at such pathological sites (termed negative contrast).

A number of factors must be considered for optimal radioimaging in humans. To maximize the efficiency of detection, a radionuclide that emits gamma energy in the 100 to 200 keV range is preferred. To minimize the absorbed radiation dose to the patient, the physical half-life of the radionuclide should be as short as the imaging procedure will allow. To allow for examinations to be performed on any day and at any time of the day, it is advantageous to have a source of the radionuclide always available at the clinical site.

A variety of radionuclides are known to be useful for radioimaging, including $^{67}$Ga, $^{99m}$Tc (Tc-99m), $^{111}$In, $^{123}$I, $^{125}$I, $^{169}$Yb or $^{186}$Re. Tc-99m is a preferred radionuclide because it emits gamma radiation at 140 keV, it has a physical half-life of 6 hours, and it is readily available on-site using a molybdenum-99/technetium-99m generator.

The sensitivity of imaging methods using radioactively-labeled peptides is much higher than other radiopharmaceuticals known in the art, since the specific binding of the radioactive peptide concentrates the radioactive signal over the area of interest. Small synthetic peptides that bind specifically to targets of interest may be advantageously used as the basis for radiotracers. This is because: 1. they may be synthesized chemically (as opposed to requiring their production in a biological system such as bacteria or mammalian cells, or their isolation from a biologically-derived substance such as a fragment of a protein); 2. they are small, hence non-target bound radiotracer is rapidly eliminated from the body, thereby reducing background (non-target) radioactivity and allowing good definition of the target; and 3. small peptides may be readily manipulated chemically to optimize their affinity for a particular binding site.

Small readily synthesized labeled peptide molecules are preferred as routinely-used radiopharmaceuticals. There is clearly a need for small synthetic labeled peptides that can be directly injected into a patient and will image pathological sites by localizing at such sites. Tc-99m labeled small synthetic peptides offer clear advantages as radiotracers for gamma scintigraphy, due to the properties of Tc-99m as a radionuclide for imaging and the utility of specific-binding small synthetic peptides as radiotracer molecules.

Radiolabeled peptides have been reported in the prior art.

Ege et al., U.S. Pat. No. 4,832,940 teach radiolabeled peptides for imaging localized T-lymphocytes.

Olexa et al., 1982, European Patent Application No. 823017009 disclose a pharmaceutically acceptable radiolabeled peptide selected from Fragment $E_1$ isolated from cross-linked fibrin, Fragment $E_2$ isolated from cross-linked fibrin, and peptides having an amino acid sequence intermediate between Fragments $E_1$ and $E_2$.

Ranby et al., 1988, PCT/US88/02276 disclose a method for detecting fibrin deposits in an animal comprising covalently binding a radiolabeled compound to fibrin.

Hadley et al., 1988, PCT/US88/03318 disclose a method for detecting a fibrin-platelet clot in vivo comprising the steps of (a) administering to a patient a labeled attenuated thrombolytic protein, wherein the label is selectively attached to a portion of the thrombolytic protein other than the fibrin binding domain; and (b) detecting the pattern of distribution of the labeled thrombolytic protein in the patient.

Lees et al., 1989, PCT/US89/01854 teach radiolabeled peptides for arterial imaging.

Sobel, 1989, PCT/US89/02656 discloses a method to locate the position of one or more thrombi in an animal using radiolabeled, enzymatically inactive tissue plasminogen activator.

Stuttle, 1990, PCT/GB90/00933 discloses radioactively labeled peptides containing from 3 to 10 amino acids comprising the sequence arginine-glycine-aspartic acid (RGD), capable of binding to an RGD binding site in vivo.

Maraganore et al., 1991, PCT/US90/04642 disclose a radiolabeled thrombus inhibitor comprising (a) a inhibitor moiety; (b) a linker moiety; and (c) and anion binding site moiety.

Rodwell et al., 1991, PCT/US91/03116 disclose conjugates of "molecular recognition units" with "effector domains".

Tubis et al., 1968, Int. J. Appl. Rad. Isot. 19:835–840 describe labeling a peptide with technetium-99m.

Sundrehagen, 1983, Int. J. Appl. Rad. Isot. 34:1003 describes labeling polypeptides with technetium-99m.

The use of chelating agents for radiolabeling polypeptides, and methods for labeling peptides and polypeptides with Tc-99m are known in the prior art and are disclosed in co-pending U.S. patent application Ser. Nos. 07/653,012 and 07/807,062, which are hereby incorporated by reference.

Although optimal for radioimaging, the chemistry of Tc-99m has not been as thoroughly studied as the chemistry of other elements and for this reason methods of radiolabeling with technetium are not abundant. Tc-99m is normally obtained as Tc-99m pertechnetate ($TcO_4^-$; technetium in the +7 oxidation state), usually from a molybdenum-99/technetium-99m generator. However, pertechnetate does not bind well to other compounds. Therefore, in order to radiolabel a peptide, Tc-99m pertechnetate must be converted to another form. Since technetium does not form a stable ion in aqueous solution, it must be held in such solutions in the form of a coordination complex that has sufficient kinetic and thermodynamic stability to prevent decomposition and resulting conversion of Tc-99m either to insoluble technetium dioxide or back to pertechnetate.

Such coordination complexes of Tc-99m (in the +1 to +6 oxidation states) are known. However, many of these complexes are inappropriate for radiolabeling due to the molecular geometry of the coordination complex. For the purpose of radiolabeling, it is particularly advantageous for the coordination complex to be formed as a chelate in which all of the donor groups surrounding the technetium ion are provided by a single chelating ligand. This allows the chelated Tc-99m to be covalently bound to a peptide through a single linker between the chelator and the peptide.

These ligands are sometimes referred to as bifunctional chelating agents having a chelating portion and a linking portion. Such compounds are known in the prior art.

Byrne et al., U.S. Pat. No. 4,434,151 describe homocysteine thiolactone-derived bifunctional chelating agents that can couple radionuclides to terminal amino-containing compounds that are capable of localizing in an organ or tissue to be imaged.

Fritzberg, U.S. Pat. No. 4,444,690 describes a series of technetium-chelating agents based on 2,3-bis (mercaptoacetamido) propanoate.

Byrne et al., U.S. Pat. Nos. 4,571,430 describe novel homocysteine thiolactone bifunctional chelating agents for chelating radionuclides that can couple radionuclides to terminal amino-containing compounds that are capable of localizing in an organ or tissue to be imaged.

Byrne et al., U.S. Pat. Nos. 4,575,556 describe novel homocysteine thiolactone bifunctional chelating agents for chelating radionuclides that can couple radionuclides to terminal amino-containing compounds that are capable of localizing in an organ or tissue to be imaged.

Davison et al., U.S. Pat. No. 4,673,562 describe technetium chelating complexes of bisamido-bisthio-ligands and salts thereof, used primarily as renal function monitoring agents.

Nicolotti et al., U.S. Pat. No. 4,861,869 describe bifunctional coupling agents useful in forming conjugates with biological molecules such as antibodies.

Fritzberg et al., U.S. Pat. No. 4,965,392 describe various S-protected mercaptoacetylglycylglycine-based chelators for labeling proteins.

Fritzberg et al., European Patent Application No. 86100360.6 describe dithiol, diamino, or diamidocarboxylic acid or amine complexes useful for making technetium-labeled imaging agents.

Dean et al., 1989, PCT/US89/02634 describe bifunctional coupling agents for radiolabeling proteins and peptides.

Flanagan et al., European Patent Application No. 90306428.5 disclose Tc-99m labeling of synthetic peptide fragments via a set of organic chelating molecules.

Albert et al., European Patent Application No. WO 91/01144 disclose radioimaging using radiolabeled peptides related to growth factors, hormones, interferons and cytokines and comprised of a specific recognition peptide covalently linked to a radionuclide chelating group.

Dean, co-pending U.S. patent application Ser. No. 07/653, 012 teaches reagents and methods for preparing peptides comprising a Tc-99m chelating group covalently linked to a specific binding peptide for radioimaging in vivo, and is hereby incorporated by reference.

(It is noted that all of these procedures would be expected to form anionic complexes of technetium in the +5 oxidation state.)

Baidoo & Lever, 1990, Bioconjugate Chem. 1:132–137 describe a method for labeling biomolecules using a bisamine bisthiol group that gives a cationic technetium complex.

It is possible to radiolabel a peptide by simply adding a thiol-containing moiety such as cysteine or mercaptoacetic acid. Such procedures have been described in the prior art.

Schochat et al., U.S. Pat. No. 5,061,641 disclose direct radiolabeling of proteins comprised of at least one "pendent" sulfhydryl group.

Dean et al., co-pending U.S. patent application 07/807, 062 teach radiolabeling peptides via attached groups containing free thiols, and is incorporated herein by reference.

Goedemans et al., PCT Application No. WO 89/07456 describe radiolabeling proteins using cyclic thiol compounds, particularly 2-iminothiolane and derivatives.

Thornback et al., EPC Application No. 90402206.8 describe preparation and use of radiolabeled proteins or peptides using thiol-containing compounds, particularly 2-iminothiolane.

Stuttle, PCT Application No. WO 90/15818 describes Tc-99m labeling of RGD-containing oligopeptides.

Again it is noted that in all of these cases the expected Tc-99m labeled species would be an anionic complex.

The binding of certain peptides to their target entities is sensitive to charge modification of the peptide. Thus, it is disadvantageous in some cases to radiolabel a peptide with Tc-99m via a chelator that will form a charged Tc-99m complex. It is advantageous in certain cases to use a chelator that will form an electrically neutral or uncharged Tc-99m complex.

This invention provides chelators for Tc-99m which may be used to prepare Tc-99 m labeled peptides in which the Tc-99m is held as a neutral chelate complex.

Some chelators said to form neutral Tc-99m complexes have been described in the prior art.

Burns et al., 1985, European Patent Application 85104959.3 describe bisamine bisthiol compounds for making small neutral Tc-99m brain imaging agents.

Kung et al., 1986, European Patent Application 86105920.2 describe bisamine bisthiol compounds for making small neutral Tc-99m imaging agents.

Bergstein et al., 1988, European Patent Application 88102252.9 describe bisamine bisthiol compounds for making small neutral Tc-99m brain imaging agents.

Bryson et al., 1988, Inorg. Chem. 27:2154–2161 describe neutral complexes of technetium-99 which are unstable to excess ligand.

Misra et al., 1989, Tet. Let. 30:1885–1888 describe bisamine bisthiol compounds for radiolabeling purposes.

Bryson et al., 1990, Inorg. Chem. 29 2948–2951 describe chelators containing two amide groups, a thiol group and a substituted pyridine that may form neutral Tc-99 complexes.

Taylor et al., 1990, J. Nucl. Med. 31:885 (Abst) describe a neutral Tc-99m complex for brain imaging.

SUMMARY OF THE INVENTION

The present invention provides scintigraphic imaging agents that are radioactively-labeled peptides. The radiolabeled peptides of the invention are comprised of peptides that specifically bind to a target in vivo and are covalently linked to a radiolabel-binding moiety wherein the moiety binds a radioisotope. It is a particular advantage in the present invention that the complex of the radiolabel-binding moiety and the radiolabel is electrically neutral, thereby avoiding interference of the covalently linked radiolabeled complex with the specific binding properties of the specific binding peptide.

In a first aspect of the present invention, radiolabeled peptides are provided capable of imaging sites within a mammalian body. The peptides are comprised of a specific binding peptide having an amino acid sequence and a radiolabel-binding moiety covalently linked to the peptide. Further, the complex of the radiolabel-binding moiety and the radiolabel is electrically neutral. In a preferred embodiment, the peptide is covalently linked to the radiolabel-binding moiety via an amino acid, most preferably glycine. In another preferred embodiment, the radiolabel is technetium-99m.

In a second embodiment, the invention provides a radiolabeled peptide for imaging sites within a mammalian body, comprising a specific binding peptide and a radiolabel-binding moiety of formula:

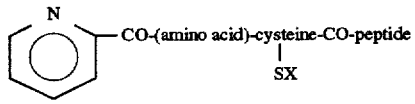

[for purposes of this invention, radiolabel-binding moieties having this structure will be referred to as picolinic acid (Pic)-based moieties]

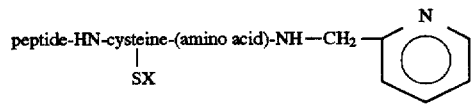

[for purposes of this invention, radiolabel-binding moieties having this structure will be referred to as picolylamine (Pica)-based moieties]

wherein X is H or a protecting group; (amino acid) is any amino acid; the radiolabel-binding moiety is covalently linked to the peptide and the complex of the radiolabel-binding moiety and the radiolabel is electrically neutral. In a preferred embodiment, the amino acid is glycine and X is an acetamidomethyl protecting group. In additional preferred embodiments, the peptide is covalently linked to the radiolabel-binding moiety via an amino acid, most preferably glycine, and the radiolabel is technetium-99m.

In yet another embodiment of the invention, a radiolabeled peptide is provided for imaging sites within a mammalian body, comprising a specific binding peptide and a bisamino bisthiol radiolabel-binding moiety covalently linked to the peptide. The bisamino bisthiol radiolabel-binding moiety in this embodiment of the invention has a formula selected from the group consisting of:

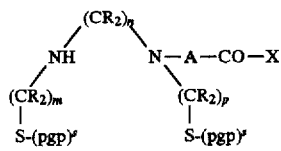

wherein each R can be independently H, CH$_3$ or C$_2$H$_5$; each (pgp)$^S$ can be independently a thiol protecting group or H; m, n and p are independently 2 or 3; A is linear or cyclic lower alkyl, aryl, heterocyclyl, combinations or substituted derivatives thereof; and X is peptide;

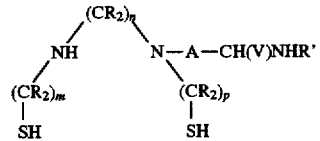

wherein each R is independently H, CH$_3$ or C$_2$H$_5$; m, n and p are independently 2 or 3; A is linear or cyclic lower alkyl, aryl, heterocyclyl, combinations or substituted derivatives thereof; V is H or CO-peptide; R' is H or peptide; provided that when V is H, R' is peptide and when R' is H, V is peptide. [For purposes of this invention, radiolabel-binding moieties having these structures will be referred to as "BAT" moieties]. In a preferred embodiment, the peptide is covalently linked to the radiolabel-binding moiety via an amino acid, most preferably glycine, and the radiolabel is technetium-99m.

Specific-binding peptides provided by the invention include but are not limited to peptides having the following sequences:

| | |
|---|---|
| formyl-MLF | |
| (VGVAPG)$_3$ amide | SEQ ID No.:1 |
| (VPGVG)$_4$ amide | SEQ ID No.:2 |
| RALVDTLKFVTQAEGAK amide | SEQ ID No.:3 |
| RALVDTEFKVKQEAGAK amide | SEQ ID No.:4 |
| PLARITLPDFRLPEIAIP amide | SEQ ID No.:5 |
| GQQHHLGGAKAGDV | SEQ ID No.:6 |
| PLYKKIIKKLLES | SEQ ID No.:7 |
| LRALVDTLK amide | SEQ ID No.:8 |
| GGGLRALVDTLK amide | SEQ ID No.:9 |
| GGGLRALVDTLKFVTQAEGAK amide | SEQ ID No.:10 |
| GGGRALVDTLKALVDTL amide | SEQ ID No.:11 |
| GHRPLDKKREEAPSLRPAPPPISGGGYR | SEQ ID No.:12 |
| PSPSPIHPAHHKRDRRQ amide | SEQ ID No.13 |
| GGGF$_D$.Cpa.YW$_D$KTFT amide | SEQ ID No.:14 |
| GGCNP.Apc.GDC | SEQ ID No.:15 |
| └─S---S─┘ | |
| [SYNRGDSTC(S-maleimido CH$_2$CH$_2$—)]$_3$N | |
| GGGLRALVDTLK amide | SEQ ID No.:16 |
| GCGGGLRALVDTLK amide | SEQ ID No.:17 |
| GCYRALVDTLKFVTQAEGAK amide | SEQ ID No.:18 |
| GC(VGVAPG)$_3$ amide | SEQ ID No.:19 |

The invention also comprises complexes of the peptides of the invention with Tc-99m and methods for radiolabeling the peptides of the invention with Tc-99m. Radiolabeled complexes provided by the invention are formed by reacting the peptides of the invention with Tc-99m in the presence of a reducing agent. Preferred reducing agents include but are not limited to dithionite ion, stannous ion, and ferrous ion. Complexes of the invention are also formed by labeling the peptides of the invention with Tc-99m by ligand exchange of a prereduced Tc-99m complex as provided herein.

The invention also provides kits for preparing the peptides of the invention radiolabeled with Tc-99m. Kits for labeling the peptide of the invention with Tc-99m are comprised of a sealed vial containing a predetermined quantity of a peptide of the invention and a sufficient amount of reducing agent to label the peptide with Tc-99m.

This invention provides methods for preparing peptides of the invention by chemical synthesis in vitro. In a preferred embodiment, peptides are synthesized by solid phase peptide synthesis.

This invention provides methods for using Tc-99m labeled peptides for imaging a site within a mammalian body by obtaining in vivo gamma scintigraphic images.

These methods comprise administering an effective diagnostic amount of a Tc-99m radiolabeled peptide of the invention and detecting the gamma radiation emitted by the Tc-99m localized at the site within the mammalian body.

Compositions of matter comprising radiolabel-binding moieties that form an electrically neutral complex with a radioisotope are also provided by the invention. In a preferred embodiment, the radioisotope is Tc-99m. Additional preferred embodiments include bisamine, bisthiol derivatives and picolinic acid and picolylamine derivatives described herein.

Specific preferred embodiments of the present invention will become evident from the following more detailed description of certain preferred embodiments and the claims.

DETAILED DESCRIPTION OF THE INVENTION

The present invention provides Tc-99m labeled peptides for imaging target sites within a mammalian body comprising an amino acid sequence covalently linked to a radiolabel-binding moiety wherein the radiolabel-binding moiety binds a radioisotope and forms an electrically neutral complex.

Labeling with Tc-99m is an advantage of the present invention because the nuclear and radioactive properties of this isotope make it an ideal scintigraphic imaging agent. This isotope has a single photon energy of 140 keV and a radioactive half-life of about 6 hours, and is readily available from a $^{99}$Mo-$^{99m}$Tc generator. Other radionuclides known in the prior art have effective half-lives which are much longer (for example, $^{111}$In, which has a half-life of 67.4 h) or are toxic (for example, $^{125}$I).

In the radiolabel binding moieties and peptides covalently linked to such moieties that contain a thiol covalently linked to a thiol protecting groups [(pgp)$^S$] provided by the invention, the thiol-protecting groups may be the same or different and may be but are not limited to:

—CH$_2$—aryl (aryl is phenyl or alkyl or alkyloxy substituted phenyl);

—CH—(aryl)$_2$, (aryl is phenyl or alkyl or alkyloxy substituted phenyl);

—C—(aryl)$_3$, (aryl is phenyl or alkyl or alkyloxy substituted phenyl);

—CH$_2$—(4-methoxyphenyl);

—CH—(4-pyridyl)(phenyl)$_2$;

—C(CH$_3$)$_3$

—9—phenylfluorenyl;

—CH$_2$NHCOR (R is unsubstituted or substituted alkyl or aryl);

—CH$_2$—NHCOOR (R is unsubstituted or substituted alkyl or aryl);

—CONHR (R is unsubstituted or substituted alkyl or aryl);

—CH$_2$—S—CH$_2$—phenyl

Preferred protecting groups have the formula —CH$_2$—NHCOR wherein R is a lower alkyl having 1 and 8 carbon atoms, phenyl or phenyl-substituted with lower alkyl, hydroxyl, lower alkoxy, carboxy, or lower alkoxycarbonyl. The most preferred protecting group is an acetamidomethyl group.

Peptides of the present invention can be chemically synthesized in vitro. Peptides of the present invention can generally advantageously be prepared on an amino acid synthesizer. The peptides of this invention can be synthesized wherein the radiolabel-binding moiety is covalently linked to the peptide during chemical synthesis in vitro, using techniques well known to those with skill in the art. Such peptides covalently-linked to the radiolabel-binding moiety during synthesis are advantageous because specific sites of covalent linkage can be determined.

Radiolabel binding moieties of the invention may be introduced into the target specific peptide during peptide synthesis. For embodiments [e.g., Pic-Gly-Cys(protecting group)-] comprising picolinic acid (Pic-), the radiolabel-binding moiety can be synthesized as the last (i.e., amino-terminal) residue in the synthesis. In addition, the picolinic acid-containing radiolabel-binding moiety may be covalently linked to the ε-amino group of lysine to give, for example, αN(Fmoc)-Lys-εN[Pic-Gly-Cys(protecting group)], which may be incorporated at any position in the peptide chain. This sequence is particularly advantageous as it affords an easy mode of incorporation into the target binding peptide.

Similarly, the picolylamine (Pica)-containing radiolabel-binding moiety [-Cys(protecting group)-Gly-Pica] can be prepared during peptide synthesis by including the the sequence [-Cys(protecting group)-Gly-] at the carboxyl terminus of the peptide chain. Following cleavage of the peptide from the resin the carboxyl terminus of the peptide is activated and coupled to picolylamine. This synthetic route requires that reactive side-chain functionalities remain masked (protected) and do not react during the conjugation of the picolylamine.

Examples of small synthetic peptides containing the Pic-Gly-Cys- and -Cys-Gly-Pica chelators are provided in the Examples hereinbelow. This invention provides for the incorporation of these chelators into virtually any peptide, resulting in a radiolabeled peptide having Tc-99m held as neutral complex.

This invention also provides specific-binding small synthetic peptides which incorporate bisamine bisthiol (BAT) chelators which may be labeled with Tc-99m, resulting in a radiolabeled peptide having Tc-99m held as neutral complex. Examples of small synthetic peptides containing these BAT chelators as radiolabel-binding moiety are provided in the Examples hereinbelow.

In forming a complex of radioactive technetium with the peptides of this invention, the technetium complex, preferably a salt of Tc-99m pertechnetate, is reacted with the peptides of this invention in the presence of a reducing agent. Preferred reducing agents are dithionite, stannous and ferrous ions; the most preferred reducing agent is stannous chloride. In an additional preferred embodiment, the reducing agent is a solid-phase reducing agent. Complexes and means for preparing such complexes are conveniently provided in a kit form comprising a sealed vial containing a predetermined quantity of a peptide of the invention to be labeled and a sufficient amount of reducing agent to label the peptide with Tc-99m. Alternatively, the complex may be formed by reacting a peptide of this invention with a preformed labile complex of technetium and another compound known as a transfer ligand. This process is known as ligand exchange and is well known to those skilled in the art. The labile complex may be formed using such transfer ligands as tartrate, citrate, gluconate or mannitol, for example. Among the Tc-99m pertechnetate salts useful with the present invention are included the alkali metal salts such as the sodium salt, or ammonium salts or lower alkyl ammonium salts.

In a preferred embodiment of the invention, a kit for preparing technetium-labeled peptides is provided. The peptides of the invention can be chemically synthesized using methods and means well-known to those with skill in the art and described hereinbelow. Peptides thus prepared are comprised of between 3 and 100 amino acid residues, and are covalently linked to a radiolabel-binding moiety wherein the radiolabel-binding moiety binds a radioisotope. An appropriate amount of the peptide is introduced into a vial containing a reducing agent, such as stannous chloride or a solid-phase reducing agent, in an amount sufficient to label the peptide with Tc-99m. An appropriate amount of a transfer ligand as described (such as tartrate, citrate, gluconate or mannitol, for example) can also be included. Technetium-labeled peptides according to the present invention can be prepared by the addition of an appropriate amount of Tc-99m or Tc-99m complex into the vials and reaction under conditions described in Example 3 hereinbelow.

Radioactively labeled peptides provided by the present invention are provided having a suitable amount of radioactivity. In forming Tc-99m radioactive complexes, it is generally preferred to form radioactive complexes in solutions containing radioactivity at concentrations of from about 0.01 millicurie (mCi) to 100 mCi per mL.

Technetium-labeled peptides provided by the present invention can be used for visualizing sites in a mammalian body. In accordance with this invention, the technetium-labeled peptides or neutral complexes thereof are administered in a single unit injectable dose. Any of the common carriers known to those with skill in the art, such as sterile saline solution or plasma, can be utilized after radiolabeling for preparing the injectable solution to diagnostically image various organs, tumors and the like in accordance with this invention. Generally, the unit dose to be administered has a radioactivity of about 0.01 mCi to about 100 mCi, preferably 1 mCi to 20 mCi. The solution to be injected at unit dosage is from about 0.01 mL to about 10 mL. After intravenous administration, imaging of the organ or tumor in vivo can take place in a matter of a few minutes. However, imaging can take place, if desired, in hours or even longer, after the radiolabeled peptide is injected into a patient. In most instances, a sufficient amount of the administered dose will accumulate in the area to be imaged within about 0.1 of an hour to permit the taking of scintiphotos. Any conventional method of scintigraphic imaging for diagnostic purposes can be utilized in accordance with this invention.

The technetium-labeled peptides and complexes provided by the invention may be administered intravenously in any conventional medium for intravenous injection such as an aqueous saline medium, or in blood plasma medium. Such medium may also contain conventional pharmaceutical adjunct materials such as, for example, pharmaceutically acceptable salts to adjust the osmotic pressure, buffers, preservatives and the like. Among the preferred media are normal saline and plasma.

The methods for making and labeling these compounds are more fully illustrated in the following Examples. These Examples illustrate certain aspects of the above-described method and advantageous results. These Examples are shown by way of illustration and not by way of limitation.

EXAMPLE 1

Synthesis of BAT Chelators

A. Synthesis of N-Boc-N'-(5-carboxypentyl)-N,N'-bis(2-methyl-2-triphenylmethylthiopropyl)ethylenediamine
a. 2-methyl-2-(triphenylmethylthio)propanal Triphenylmethylmercaptan (362.94 g, 1.31 mol, 100 mol %) dissolved in anhydrous THF (2 L) was cooled in an ice bath under argon. Sodium hydride (60% in oil; 54.39 g, 1.35 mol, 104 mol %) was added in portions over 20 min. 2-bromo-2-methylpropanal (206.06 g, 1.36 mol, 104 mol %; see Stevens & Gillis, 1957, J. Amer. Chem. Soc. 79: 3448–51) was then added slowly over 20 min. The reaction mixture was allowed to warm to room temperature and stirred for 12 hours. The reaction was quenched with water (1 L) and extracted with diethyl ether (3x 1 L). The ether extracts were combined, washed with saturated NaCl solution (500 mL), dried over $Na_2SO_4$ and filtered. The solvent was removed under reduced pressure to afford a thick orange oil. The crude oil was dissolved in toluene (200 mL) and diluted to 2 L with hot hexanes. The mixture was filtered through a sintered glass funnel and cooled at −5° C. for 12 hours. The white crystalline solid which formed was removed by filtration to afford 266.36 g (59% yield) of the title compound. The melting point of the resulting compound was determined to be 83°–85° C. Nuclear magnetic resonance characterization experiments yielded the following molecular signature:

$^1$H NMR(300 $MH_z$, $CDCl_3$): δ 1.24(s, 6H, 2$CH_3$), 7.2–7.35 (m, 9H), 7.59–7.62 (m,6H), 8.69 (s, H, —COH)

$^{13}$C NMR (75 $MH_z$, $CDCl_3$): δ 22.86, 55.66, 67.48, 126.85, 127.75, 129.72, 144.79, 197.31.

b. N,N'-Bis(2-methyl-2-(triphenylmethylthio)propyl) ethylenediamine.

Ethylenediamine (1.3 mL, 0.0194 mol, 100 mol %) was added to 2-methyl-2-(triphenylmethylthio)propanal (13.86 g, 0.0401 mol, 206 mol %) dissolved in methanol (40 mL) and anhydrous THF (40 mL) under argon, and the pH was adjusted to pH 6 by dropwise addition of acetic acid. The solution was stirred for 20 min at 20° C. Sodium cyanoborohydride (1.22 g, 0.0194 mol, 100 mol %) was added and the reaction was stirred at room temperature for 3 hours. Additional sodium cyanoborohydride (1.08 g) was added and the reaction was stirred at 20° C. for 17 hours. A final portion of sodium cyanoborohydride (1.02 g) was added and the reaction heated at reflux under argon for 6 hours. The reaction was quenched with 0.5M HCl (100 mL) and extracted with ethyl acetate (2x 100 mL). The organic extracts were combined, sequentially washed with 2M NaOH (60 mL), saturated NaCl solution (60 mL), dried ($Na_2SO_4$), and filtered. The solvent was removed under reduced pressure to give 16.67 g of crude product which was crystallized from toluene/hexanes to afford 10.20 g (73% yield) of white crystals of the title compound. The melting point of the resulting compound was determined to be 83°–86° C. FABMS analysis yielded an m/z of 721 (MH+). Nuclear magnetic resonance characterization experiments yielded the following molecular signature:

$^1$H NMR (300 $MH_z$, $CDCl_3$): δ 1.12 (s, 12H, 4 $CH_3$), 1.64 (s, 4H, N-$CH_2$-C(Me)$_2$-S), 2.52 (s, 4H, N-$CH_2$-$CH_2$-N), 5.31 (S, 2H, 2-NH), 7.12–7.30 (m, 18H, Ar), 7.62–7.65 (m, 12H, Ar).

c. N-(5-carboethoxypentyl)-N,N'-bis(2-methyl-2-triphenylmethylthiopropyl)ethylenediamine $K_2CO_3$ (1.92 g, 13.9 mmol, 100 mol %) was added to N,N'-bis(2-methyl-2-triphenylmethylthiopropyl) ethylenediamine (10.03 g, 13.9 mmol) in $CH_3CN$ (60 mL), followed by ethyl 5-bromovalerate (3.30 mL, 20.8 mmol, 150 mol %). The reaction was heated at reflux under argon overnight. The solution was then concentrated to a paste and partitioned between 0.25M KOH (100 mL) and ethyl acetate (100 mL). The aqueous layer was extracted with ethyl acetate (1x 50 mL) and the combined ethyl acetate layers were washed with 50 mL water and NaCl solution (2x 50 mL), dried with Na₂SO₄ and concentrated to an orange oil. Purification by flash chromatography (300 g flash silica, 100% CHCl₃ to 5% MeOH/CHCl₃) gave pure title compound (7.75 g, 66% yield). FABMS analysis yielded an (MH+) of 849 (compared with a calculated molecular weight of 849.24 for the compound $C_{55}H_{64}N_2O_2S_2$).

d. N-Boc-N'-(5-carboxypentyl)-N,N'-bis(2-methyl-2-triphenylmethylthiopropyl) ethylenediamine 1M KOH (25 mL, 25.0 mmol, 274 mol %) was added to N-(5-carboethoxypentyl)-N,N'-bis(2-methyl-2-triphenylmethylthiopropyl)ethylenediamine(7.75 g, 9.13 mmol) in dioxane (200 mL), followed by water (250 mL). Dioxane was then added dropwise with stirring until a homogeneous solution was obtained. The reaction was heated at a slow reflux overnight. Most of the dioxane was removed by rotary evaporation and the pH of solution was adjusted to ~7–8 with 1M $KH_2PO_4$ and saturated $NaHCO_3$. The solution was then extracted with ethyl acetate (3x 75 mL) and the combined organic layers were washed with NaCl solution (50 mL), dried with Na₂SO₄ and concentrated to a foam/solid (6.35 g, 85% yield).

To the crude product from the above reaction was added $(BOC)_2O$ (3.35 g, 15.4 mmol, 200 mol %), $CH_3CN$ (50 mL) and methylene chloride (50 mL), followed by triethylamine (1.0 mL, 7.2 mmol, 93 mol %). The reaction was stirred at room temperature under argon overnight. The reaction solution was then concentrated and partitioned between water (100 mL) and ethyl acetate (50 mL). The aqueous layer was extracted with ethyl acetate (1x 50 mL) and the combined ethyl acetate layers were washed with 5% citric acid and NaCl solution (50 mL each), then dried (Na₂SO₄) and concentrated to an orange oil. Purification by flash chromatography (200 g flash silica, 100% CDCl₃ to 5% methanol/chloroform) gave pure title compound (2.58 g, 36% yield). FABMS analysis gave an (MH+) of 921 (compared with the calculated value of 921.31 for the compound $C_{58}H_{68}N_2O_4S_2$).

B. Synthesis of N-Boc-N'-(5-carboxypentyl)-N,N'-bis-[2-(4-methoxybenzylthio)-2-methylpropyl]ethylenediamine a. N,N'-bis-[2-(4-methoxybenzylthio)-2-methylpropyl]-ethylenediamine A solution of N,N'-bis(2-mercapto-2-methylpropyl) ethylene diamine (11.23 g, 47.5 mmol; see, DiZio et al., 1991, Bioconjugate Chem 2:353 and Corbin et al., 1976, J. Org. Chem. 41:489) in methanol (500 mL) was cooled in ice/water bath and then saturated with gaseous ammonia over 45 min. To this was added 4-methoxybenzyl chloride (17.0 mL, 125 mmol, 264 mol %). The reaction was allowed to warm to room temperature overnight with stirring under argon. The solution was concentrated to a paste and then partitioned between diethyl ether (150 mL) and 0.5M KOH (200 mL). The aqueous layer was further extracted with diethyl ether (2x 50 mL). The combined organic layers were washed with NaCl solution and concentrated to a clear colorless oil. The oil dissolved in diethyl ether (200 mL) and then acidified with 4.0M HCl in dioxane until no further precipitation was seen. The white precipitate was collected by filtration and washed with diethyl ether. The white solid was recrystallized from hot water at a pH of ~2. The product was collected by filtration to afford 29.94 g as a mix of mono- and di- HCl salts. The HCl salts were partitioned between 1M KOH (100 mL) and ethyl acetate (100 mL). The aqueous was extracted with ethyl acetate (2x 30 mL) and the combined organic layers were washed with NaCl solution, dried with Na₂SO₄ and concentrated to give pure product as the free base as a light yellow oil (18.53 g, 82% yield).

Nuclear magnetic resonance characterization experiments yielded the following molecular signature:

$^1$H NMR (300 MHz, CDCL₃): δ 7.25 (d, 4H, J=9), 6.83 (d, 4H, J=9), 3.78 (s, 6H), 3.67 (s, 4H), 2.63 (s, 4H), 2.56 (s, 4H), 1.34 (s, 12H).

b. N-(5-carboethoxypentyl)-N,N'-bis-[2-(4-methoxybenzylthio)-2-methylpropyl]ethylenediamine To N,N'-bis-[2-(4-methoxybenzylthio)-2-methylpropyl]-ethylenediamine (4.13 g, 8.66 mmol) in $CH_3CN$ (50 mL) was added $K_2CO_3$ (1.21 g, 8.75 mmol, 101 mol %) followed by ethyl 5-bromovalerate (2.80 mL, 17.7 mmol, 204 mol %). The reaction was stirred at reflux overnight and was then concentrated to a paste in vacuo. The residue was partitioned between ethyl acetate (100 mL) and 0.5M KOH (100 mL). The aqueous layer was extracted with ethyl acetate (1x 50 mL) and the combined organic layers were washed with NaCl solution (50 mL), dried with Na₂SO₄ and concentrated to a yellow oil (~6 g). Purification by normal-phase preparative HPLC (100% CHCl₃ to 5% methanol/chloroform over 25 min.) afforded pure title compound (1.759 g, 34% yield). FABMS analysis gave an (MH+) of 605 (compared with the value of 604.90 calculated for $C_{33}H_{52}N_2O_4S_2$). Nuclear magnetic resonance characterization experiments yielded the following molecular signature:

$^1$H NMR (300 mH$_z$, CDCl₃): δ 7.25 (d, 4H, J=8.5), 6.83 (d, 4H, J=8.5), 4.13 (q, 2H, J=7), 3.793 (s, 3H), 3.789 (s, 3H), 3.74 (s, 2H), 3.67 (s, 2H), 2.6 (m, 10H), 2.31 (t, 2H, J=7), 1.6 (m, 2H), 1.5 (m 2H), 1.34 (s 12H), 1.28 (t, 3H, J=7).

c. N-Boc-N'-(5-carboxypentyl)-N,N'-bis-[2-(4-methoxybenzylthio)-2-methylpropyl]ethylenediamine To N-(5-carboethoxypentyl)-N,N'-bis-[2-(4-methoxybenzylthio)-2-methylpropyl]ethylenediamine (586 mg, 0.969 mmol) in THF (40 mL) was added water (30 mL) and 1M KOH (2.5 mL, 2.5 mmol, 260 mol %). The homogeneous solution was heated to a slow reflux overnight. The solution was then cooled to room temperature and the THF was removed under rotary evaporation. The residue was diluted to 50 mL with H₂O and the pH was adjusted to ~2–3 with 1M HCl. The solution was extracted with ethyl acetate (3x 30 mL) and the combined organic layers were washed with NaCl solution (50 mL), dried with Na₂SO₄ and concentrated to give crude acid (422 mg, 75% yield).

To the crude product from the above reaction was added $CH_3CN$ (40 mL) and $(BOC)_2O$ (240 mg, 1.10 mmol, 150 mol %) followed by triethylamine (0.200 mL, 1.43 mmol, 196 mol %). The homogenous solution stiffed at room temperature overnight under argon. The solution was then concentrated to a paste and partitioned between ethyl acetate (25 mL) and 1M KH2PO₄ (25 mL). The organic layer was washed with 5% citric acid (2x 25 mL) and NaCl solution (25 mL), dried with Na₂SO₄ and concentrated to a yellow oil. Purification by flash chromatography (50 mL flash silica gel, 100% chloroform to 15% methanol/chloroform) gave pure title compound (344 mg, 70% yield). FABMS analysis gave an (MH+) of 677 (compared to the value of 676.97 calculated for the compound $C_{36}H_{56}N_2O_6S_2$). Nuclear magnetic resonance characterization experiments yielded the following molecular signature:

$^1$H NMR (300 MHz, CDCl₃): δ 7.20 (d, 4H, J=7), 6.79 (d, 4H, J=7), 3.75 (S, 3H), 3.74 (S, 3H), 3.68 (M, 4H), 3.35 (M, 4H), 2.65 (M, 2H), 2.53 (M, 4H), 2.31 (M, 2H), 1.59 (M, 2H), 1.43 (S, 11H), 1.30 (S, 6H), 1.26 (S, 6H)

EXAMPLE 2

Solid Phase Peptide Synthesis

Solid phase peptide synthesis (SPPS) was carried out on a 0.25 millimole (mmole) scale using an Applied Biosystems Model 431A Peptide Synthesizer and using 9-fluorenylmethyloxycarbonyl (Fmoc) amino-terminus protection, coupling with dicyclohexylcarbodiimide/hydroxybenzotriazole or 2-(1H-benzo-triazol-1-yl)-1,1,3,3-tetramethyluronium hexafluorophosphate/hydroxybenzotriazole (HBTU/HOBT), and using p-hydroxymethylphenoxymethyl-polystyrene (HMP) resin for carboxyl-terminus acids or Rink amide resin for carboxyl-terminus amides. Resin-bound products were routinely cleaved using a solution comprised of trifluoroacetic acid, water, thioanisole, ethanedithiol, and triethylsilane, prepared in ratios of 100:5:5:2.5:2 for 1.5–3 h at room temperature.

Where appropriate αN-formyl groups were introduced by treating the cleaved, deprotected peptide with excess acetic anhydride in 98% formic acid and stirring for about 18 hours followed by HPLC purification. Where appropriate N-terminal acetyl groups were introduced by treating the free N-terminal amino peptide bound to the resin with 20% v/v acetic anhydride in NMP (N-methylpyrrolidinone) for 30 min. Where appropriate BAT ligands were introduced either by using the appropriate BAT acid as the last residue to be coupled during SPPS or by treating the N-terminus free and no peptide bound to the resin with the BAT acid/diisopropylcarbodiimide/N-hydroxysuccinimide in NMP. Where appropriate, Cys—Cys disulfide bond cyclizations were performed by treating the precursor cysteine-free thiol peptides at 0.1 mg/mL in pH 7 buffer with aliquots of 0.006M $K_3Fe(CN)_6$ until a stable yellow color persisted. The excess oxidant was reduced with excess cysteine, the mixture was lyophilized and then purified by HPLC.

Crude peptides were purified by preparative high pressure liquid chromatography (HPLC) using a Waters Delta Pak C18 column and gradient elution using 0.1% trifluoroacetic acid (TFA) in water modified with acetonitrile. Acetonitrile was evaporated from the eluted fractions which were then lyophilized. The identity of each product was confirmed by fast atom bombardment mass spectroscopy (FABMS).

EXAMPLE 3

A General Method for Radiolabeling with Tc-99m 0.1 mg of a peptide prepared as in Example 2 was dissolved in 0.1 mL of water or 50 mM potassium phosphate buffer (pH=5, 6 or 7.4). Tc-99m gluceptate was prepared by reconstituting a Glucoscan vial (E.I. DuPont de Nemours, Inc.) with 1.0 mL of Tc-99m sodium pertechnetate containing up to 200 mCi and allowed to stand for 15 minutes at room temperature. 25 µl of Tc-99m gluceptate was then added to the peptide and the reaction allowed to proceed at room temperature or at 100° C. for 15–30 min and then filtered through a 0.2 µm filter.

The Tc-99m labeled peptide purity was determined by HPLC using the conditions described in the Footnotes in Table I. Radioactive components were detected by an in-line radiometric detector linked to an integrating recorder. Tc-99m gluceptate and Tc-99m sodium pertechnetate elute between 1 and 4 minutes under these conditions, whereas the Tc-99m labeled peptide eluted after a much greater amount of time.

The following Table illustrates successful Tc-99m labeling of peptides prepared according to Example 2 using the method described herein.

| Peptides | FABMS MH+ | Radiochemical Yield(%)* | HPLC $R_T$ (min)** |
|---|---|---|---|
| formyl-MLFC$_{Acm}$G.Pica | 760 | 100[2] | 10.9, 11.5, 12.2[1] |
| Pic.GC$_{Acm}$(VGVAPG)$_3$amide | 1795 | 100[2] | 12.4[3] |
| Pic.GC$_{Acm}$(VPGVG)$_4$amide | 1992 | 100[2] | 12.0[1] |
| Pic.GC$_{Acm}$RALVDTLKFVTQAEGAKamide | 2183 | 95[2] | 17.2[3] |
| Pic.GC$_{Acm}$RALVDTEFKVKQEAGAKamide | 2226 | 96[2] | 15.5[3] |
| Pic.GC$_{Acm}$PLARITLPDFRLPEIAIPamide | 2368 | 92[2] | 19.2[1] |
| Pic.GC$_{Acm}$GQQHHLGGAKAGDV | 1838 | 48[2] | 12.8–16.6[2] |
| Pic.GC$_{Acm}$PLYKKIIKKLLES | 1910 | 81[2] | 10.7–14.5[2] |
| Pic.GC$_{Acm}$LRALVDTLKamide | 1363 | 92[6] | 13.0–14.5[2] |
| Pic.GC$_{Acm}$GGGLRALVDTLKamide | 1535 | 100[1] | 15.6[2] |
| Pic.GC$_{Acm}$GGGLRALVDTLKFVTQAEGAKamide | 2354 | 92[5] | 15.1[2] |
| Pic.GC$_{Acm}$GGGRALVDTLKALVDTLamide | 2035 | 86[6] | 14.5[2] |
| Pic.GC$_{Acm}$GHRPLDKKREEAPSLRPAPPPISGGGYR | 3377 | 94[6] | 11.3[2] |
| Pic.GC$_{Acm}$PSPSPIHPAHHKRDRRQamide | 2351 | 94[6] | 11.2, 14.4[2] |
| Pic.GC$_{Acm}$GGGF$_D$.Cpa.YW$_D$KTFTamide | 1681 | 98[3] | 13.8–16.8[2] |
| Pic.GC$_{Acm}$GGCNP.Apc.GDC<br>└ S — S ┘ | 1217 | 69[2] | 6.6–13.7[2] |
| Pic.SC$_{Acm}$SYNRGDSTC(S-maleimido)CH$_2$CH$_2$—]$_3$N* | 4488 | 99[2] | 10.4, 11.2[2] |
| Pic.GC$_{Mob}$GGGLRALVDTLKamide | 1471 | 100[6] | 11.9[4] |
| Pic.GCGGGLRALVDTLKamide | 1350 | 100[6] | 11.2, 11.6[4] |
| Pic.GCYRALVDTLKFVTQAEGAKamide | 2275 | 95[3] | 18.6, 19.1[2] |
| Pic.GC(VGVAPG)$_3$amide | 1724 | 95[3] | 17.3[2] |
| BAT-RALVDTLKFVTQAEGAKamide | 2165 | 98[3] | 19.0[2] |

*Superscripts refer to the following labeling conditions
1. The peptide is dissolved in 50 mM potassium phosphate buffer (pH 7.4) and labeled at room temperature.
2. The peptide is dissolved in 50 mM potassium phosphate buffer (pH 7.4) and labeled at 100° C.
3. The peptide is dissolved in water and labeled at room temperature.
4. The peptide is dissolved in water and labeled at 100° C.
5. The peptide is dissolved in 50 mM potassium phosphate buffer (pH 6.0) and labeled at 100° C.
6. The peptide is dissolved in 50 mM potassium phosphate buffer (pH 5.0) and labeled at room temperature.
**HPLC methods (indicated by superscript after $R_T$):

-continued

| Peptides | FABMS MH+ | Radiochemical Yield(%)* | HPLC $R_T$ (min)** |
|---|---|---|---| general:
solvent A = 0.1% $CF_3COOH/H_2O$
solvent $B_{70}$ = 0.1% $CF_3COOH/70\%$ $CH_3CN/H_2O$
solvent $B_{90}$ = 0.1% $CF_3COOH/90\%$ $CH_3CN/H_2O$
solvent flow rate = 1 mL/min
Vydak column = Vydak 218TP54 RP-18, 5μ × 220 mm × 4.6 mm analytical column with guard column
Brownlee column = Brownlee Spheri-5 RP-18, 5μ × 220 mm × 4.6 mm column
Method 1: Brownlee column 100% A to 100% $B_{70}$ in 10 min
Method 2: Vydak column 100% A to 100% $B_{90}$ in 10 min
Method 3: Vydak column 100% A to 100% $B_{70}$ in 10 min
Method 4: Brownlee column 100% A to 100% $B_{90}$ in 10 min
Single-letter abbreviations for amino acids can be found in G. Zubay, Biochemistry (2d. ed.), 1988 (MacMillen Publishing: New York) p. 33; Ac = acetyl; Pic = picolinoyl (pyridine-2-carbonyl); Acm = acetamidomethyl; Mob = 4-methoxybenzyl; Pica = picolylamine (2-(aminomethyl)pyridine); Apc = L-[S-(3-aminopropyl)cysteine; $F_D$ = D-phenylalanine; $Y_D$ = D-tyrosine; Cpa = L-(4-chlorophenyl)alanine; BAT = $HSC(CH_3)_2CH_2NHCH_2CH_2N(CH_2CH_2CH_2CH_2CO-)CH_2C(CH_3)_2SH$
*The structure of this compound is as follows:

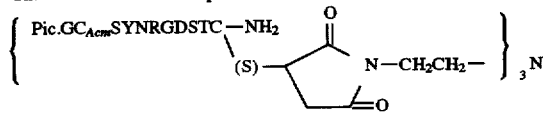

It should be understood that the foregoing disclosure emphasizes certain specific embodiments of the invention and that all modifications or alternatives equivalent thereto are within the spirit and scope of the invention as set forth in the appended claims.

---

What is claimed is:

1. A composition of matter comprising a radiolabel-binding moiety of formula:

[pyridyl ring]—CO-(amino acid)-cysteine-COOH
                        |
                        SX H₂N-cysteine-(amino acid)-NH—CH₂—[pyridyl ring]
     |
     SX wherein X=H or a protecting group;

(amino acid)=any amino acid; and wherein the radiolabel-binding moiety forms a complex with a radioisotope, and the complex of the radiolabel-binding moiety and the radioisotope is electrically neutral.

2. The composition of matter of claim 1 wherein the (amino acid) is glycine and wherein X is an acetamidomethyl protecting group.

* * * * *

UNITED STATES PATENT AND TRADEMARK OFFICE
CERTIFICATE OF CORRECTION

PATENT NO. : 5,720,934

DATED : February 24, 1998

INVENTOR(S) : Dean et al.

It is certified that error appears in the above-identified patent and that said Letters Patent are hereby corrected as shown below:

At col. 3, line 58, please replace "European" with –International–.

At col. 4, line 38, please replace "Tc-99 m" with –Tc-99m–.

At col. 6, line 14, please replace "peptide" with –CO-peptide–.

At col. 7, line 66, please replace "amino acid" with –peptide–.

At col. 12, line 49, please replace "KH2PO$_4$" with –KH$_2$PO$_4$–.

At col. 13, line 24, please replace "and no peptide" with –amino peptide–.

Signed and Sealed this

Second Day of June, 1998

Attest:

BRUCE LEHMAN

*Attesting Officer*

*Commissioner of Patents and Trademarks*